United States Patent
Dal Farra et al.

(10) Patent No.: US 8,765,689 B2
(45) Date of Patent: Jul. 1, 2014

(54) ANTI-AGEING PEPTIDES MODULATING SURVIVIN AND COMPOSITIONS INCLUDING SAME

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 94 days.

(21) Appl. No.: 13/521,645

(22) PCT Filed: Jan. 13, 2011

(86) PCT No.: PCT/FR2011/000017
§ 371 (c)(1),
(2), (4) Date: Nov. 12, 2012

(87) PCT Pub. No.: WO2011/086296
PCT Pub. Date: Jul. 21, 2011

(65) Prior Publication Data
US 2013/0336904 A1    Dec. 19, 2013

(30) Foreign Application Priority Data
Jan. 14, 2010  (FR) ..................... 10 00134

(51) Int. Cl.
| | |
|---|---|
| *A61K 38/08* | (2006.01) |
| *A61K 38/10* | (2006.01) |
| *A61K 8/64* | (2006.01) |
| *C07K 7/06* | (2006.01) |
| *C07K 7/08* | (2006.01) |
| *A61Q 19/00* | (2006.01) |
| *A61Q 19/08* | (2006.01) |
| *A61Q 5/00* | (2006.01) |
| *A61Q 7/00* | (2006.01) |
| *A61Q 17/04* | (2006.01) |

(52) U.S. Cl.
CPC ... *C07K 7/06* (2013.01); *C07K 7/08* (2013.01); *A61Q 19/00* (2013.01); *A61Q 19/08* (2013.01); *A61Q 5/00* (2013.01); *A61Q 7/00* (2013.01); *A61Q 17/04* (2013.01); *A61K 38/08* (2013.01); *A61K 38/10* (2013.01); *A61K 8/64* (2013.01)
USPC ......... 514/21.8; 514/1.1; 514/18.6; 514/18.8; 514/20.7; 514/21.5; 514/21.6; 514/21.7; 530/327; 530/328; 530/329; 530/330

(58) Field of Classification Search
CPC ............ C07K 7/06; C07K 7/08; A61Q 19/00; A61Q 19/08; A61Q 5/00; A61Q 7/00; A61Q 17/04; A61K 38/08; A61K 38/10; A61K 8/64
USPC .......... 530/327, 328, 329, 330; 514/1.1, 18.6, 514/18.8, 20.7, 21.5, 21.6, 21.7, 21.8
See application file for complete search history.

(56) References Cited

FOREIGN PATENT DOCUMENTS

| CH | 706016 | * 7/2013 | ............... A61K 8/64 |
|---|---|---|---|
| WO | WO 2007/039192 | 4/2007 | |

OTHER PUBLICATIONS

CH706016 machine translation of abstract, Jul. 2013.*
CH706016 machine translation of patent, Jul. 2013.*
Effects of Aging on the Skin, from Merck manual, p. 1. Accessed Apr. 9, 2012.*
Chronic effects of Sunlight from Merck manual, pp. 1-2. Accessed Aug. 23, 2012.*
Alopecia from Merck manual, pp. 1-5. Accessed Jul. 2, 2013.*
Search Report, PCT/FR2011/000017, Apr. 8, 2011, ISP Investments Inc.
Marconi Alessandra et al: Survivin identifies keratinocyte stem cells and is Downnregulated by anti-beta 1 integrin during anoikis[11] Stem Cells (Miamisburg) Jan. 2007.
Xu Zhenjie et al: INCENP-aurora B interactions modulate kinase activity and chromosome passenger complex locatation.Journal of Cell Biology. Nov. 2009.

* cited by examiner

*Primary Examiner* — Julie Ha
(74) *Attorney, Agent, or Firm* — Thompson Hine L.L.P.

(57) ABSTRACT

Peptide compounds of the general formula (I) $R_1$-$(AA)_n$-$X_1$—$X_2$-Arg-Glu-Met-Asn-Trp-$X_3$-$(AA)_p$-$R_2$ modulating the survivin protein are described. Furthermore, cosmetic or pharmaceutical compositions, including at least one peptide of the general formula (I), in a physiologically acceptable medium are described. Additionally, methods for treating the cutaneous signs of ageing and photo-ageing, treating the skin against external aggressions, and limiting hair loss and/or stimulating hair growth are described.

14 Claims, 1 Drawing Sheet

Protective effect of a peptide compound according to this invention on keratinocytes (RA fraction enriched with epidermal adult stem cells) subjected to UVB radiation

ANTI-AGEING PEPTIDES MODULATING SURVIVIN AND COMPOSITIONS INCLUDING SAME

CROSS REFERENCE TO RELATED APPLICATIONS

This application is the national stage of PCT Application No. PCT/FR2011/000017 filed Jan. 13, 2011, which claims priority from French Patent Application No. 10 00134, filed Jan. 14, 2010, the entire disclosures of which are hereby incorporated in their entirety.

The present invention pertains to the cosmetic and pharmaceutical fields. The present invention relates to peptide compounds of the general formula (I) $R_1$-$(AA)_n$-$X_1$—$X_2$-Arg-Glu-Met-Asn-Trp-$X_3$-$(AA)_p$-$R_2$, which are modulators of the Survivin protein, and to their use in cosmetics and/or pharmaceutics in order to (i) prevent and/or correct the signs of skin aging and photoaging in the skin and keratinous appendages, (ii) prevent and/or limit hair loss and/or stimulate hair growth, and (iii) protect the skin against external aggressions, including those due to UV radiation.

Aging corresponds to the set of physiological and psychological processes that alter the structure and functions of the body after a certain age. There are two types of aging, namely, intrinsic aging on the one hand, and extrinsic aging on the other hand. Intrinsic aging is due to genetic factors, biochemical changes that occur during conditions of fatigue, stress, hormonal changes such as during pregnancy, etc. Extrinsic aging, on the other hand, is caused by to environmental factors to which the body is subjected throughout life, such as pollution, sun, diseases, etc. This is a slow and gradual process that affects every cell in the body by various means and manifests itself in different ways. For example, in the case of the skin, its appearance is modified by various types of internal or external aggression, and the emergence of wrinkles and fine lines, hyper- or hypo-pigmentation spots, dryness or even dehydration of the skin, thinning of the skin, elastosis, blemishes, age spots, . . . , can be observed. In the case of the hair, aging manifests itself mainly by whitening (greying) of the hair, but also by a loss of hair density, thinning of the hair, which among other things, can lead to even more extensive hair fall, known as alopecia.

In mammals and especially humans, the skin and eyes are organs that are subjected to continuous renewal. For example, the skin surface desquamation phenomenon must be compensated for by epidermis renewal, which is ensured by the keratinocytes in the basal layer, which actively divide and differentiate into cells of the stratum corneum. The hair's renewal cycle can also be divided into three distinct phases known as the anagen, catagen and telogen phases. It is during the telogen phase that a new hair bulb is formed and initiates a new cycle of hair growth. These renewal activities, but also skin or nail repair activities in the case of damage such as that caused by UV radiation or wounds, rely on the existence of somatic stem cells known as epidermal adult stem cells in the skin, and follicular adult stem cells in the case of hair. These cells are somewhat unique in that they have significant self-renewal and differentiation capabilities. They have been identified within the basal layer by means of a set of molecular markers such as β1-integrin, α6-integrin, keratin K15, keratin K19 . . . . Cell proliferation and differentiation are processes that are dependent on the cell cycle. The mechanisms that control correct cell cycle functioning are based essentially on a set of complementary protein structures, such as the "chromosomal passenger complex" (CPC). CPC plays a key role in both mitotic progression and at the cytokinesis stage. CPC consists in a set of four proteins which are: INCENP (Inner Centromere Protein), Borealin, Aurora B kinase and Survivin. Survivin is expressed at point G2/M in a cell-cycle dependent manner. It has been shown that the deactivation of Survivin or Aurora B kinase by siRNA induces, inter alia, major mitotic defects (Lens S M et al., EMBO. J. 2003, 22 (12): 2934-47). Other experiments have demonstrated the key role of Survivin, of its Crm-1 carrier (or exportin 1) and its CPC partners during the control of mitosis. Lastly, other studies have allowed Survivin to be classified as being a molecule belonging to the apoptosis-inhibitor protein family, also known as the "inhibitor of apoptosis protein" (IAP). Indeed, Survivin seems to protect cells from apoptosis by inhibiting the signaling pathway of caspase-9. However, it appears that the mitotic activity of Survivin predominates over its anti-apoptotic activity. The presence of higher levels of Survivin in adult stem cells located in the basal layer of the epidermis of young subjects as compared to that present in the epidermis of elderly subjects has been established. In addition, it has been proven that fetal tissues contain large amounts of Survivin, whereas it is virtually absent in differentiated tissues (Adida et al., Am J Pathol. 1998, 152:43-49). This is how the correlation between the amount of Survivin in said stem cells and aging of the skin was established (Marconi et al., Stem Cells 2007; 25: 149-55). And it is on the basis of these findings that the Applicant, surprisingly, has demonstrated that the peptide compounds of the following general formula (I):

$R_1$-$(AA)_n$-$X_1$—$X_2$-Arg-Glu-Met-Asn-Trp-$X_3$-$(AA)_p$-$R_2$ are very good modulators of Survivin and thereby of the CPC complex, and have a significant effect on the treatment and/or prevention of the signs of skin aging, on the protection of the skin against external aggressions such as UV radiation, and on hair loss.

No compound having this type of action has so far been proposed for the treatment of aging or hair loss. Certain types of peptide compound had been proposed as anti-tumor treatments by modulating the expression of Survivin (patents EP1913947, EP 1931376). Other treatments using Survivin inhibitor peptides have been disclosed, for example, to inhibit hair growth (patent EP1841401), or to assist in the identification of tumors (patent EP2119726), etc. Patent application FR 2 932 086, for its part, describes cosmetic agents selected from extracts of *Coleus Forskolii, Lepechinia caulescens, Limnophila conferta, Daniellia oliveri, Nostoc Commune, Scenedesmus dimorphus, Curcuma longa* or *Crocus sativus*, as Survivin promoter agents for preventing or delaying the onset of signs of skin aging, or for promoting hair growth. However, no treatment using compounds that modulate Survivin (and CPC proteins) has been proposed to (i) combat signs of skin aging, (ii) protect the skin against external aggressions, including those due to UV radiation, and (iii) limit hair loss or activate hair growth. Nonetheless, there is a real need for innovating treatments in this field. Thus, the peptide compounds as described in the present invention can provide a new type of effective treatment to combat aging, by acting directly on the immediate environment of epidermal adult stem cells in order to protect them and enable them to best ensure their role in the process of renewing and protecting skin cells. Peptide compounds have the advantage of protecting the environment of the epidermal adult stem cells and of modulating the amount of Survivin in these cells, but without increasing their clonogenicity. In general, the peptides according to the present invention contribute to the preservation of the "Stemness Potential" of stem cells, by protecting their close environment and limiting their possible exhaustion. Through its protective action on epidermal and follicular adult stem cells, the compound according to the present invention can also prevent hair loss and stimulate hair growth.

Therefore, a first object of the present invention is to provide a peptide compound of the following general formula (I):

Where
$X_1$ is a leucine, alanine, or absent,
$X_2$ is a lysine, proline, or absent,
$X_3$ is a leucine, aspartic acid, tyrosine, phenylalanine, or absent,
AA is any amino acid, and n and p are integers between 0 and 2,
$R_1$ is the N-terminal amino acid's primary amine function, whether free or substituted with group of the acyl type having a $C_1$ to $C_{30}$ alkyl chain, whether saturated or unsaturated, which is selected from an acetyl group or an aromatic group, where the latter is selected from a group of the benzoyl, tosyl, or benzyloxycarbonyl type,
$R_2$ is the hydroxyl group of the C-terminal amino acid's carboxyl function, whether unsubstituted or substituted with a group that is selected from a $C_1$ to $C_{30}$ alkyl chain, or a $NH_2$, NHY or NYY group, where Y is a $C_1$ to $C_4$ alkyl chain,
said sequence of general formula (I) consisting of 5 to 12 amino acid residues, and where said sequence of general formula (I) can include derivatives or substitutions of the AA, $X_1$, $X_2$, or $X_3$ amino acids with other chemically equivalent amino acids.

A second object of the present invention is to provide a cosmetic composition, which comprises as the active ingredient said peptide compound of formula (I).

Furthermore, a third object of the present invention is the use of a cosmetic composition comprising said peptide compound of formula (I) in order to (i) prevent and/or treat the signs of skin aging and photo-aging and promote tissue regeneration, (ii) protect the skin against external aggressions, in particular those due to UV radiation, (iii) restore an optimum level of Survivin and ensure better functioning of the "Chromosomal Passenger Complex", and (iv) prevent and/or limit hair loss and/or stimulate hair growth.

Lastly, a fourth object of the present invention is to provide a method for the cosmetic treatment of skin or keratinous appendages to be treated, using the composition comprising said peptide compound of formula (I).

The first object of the present invention relates to a peptide compound of the general formula (I):

$$R_1\text{-}(AA)_n\text{-}X_1\text{—}X_2\text{-Arg-Glu-Met-Asn-Trp-}X_3\text{-}(AA)_p\text{-}R_2 \quad (I)$$

where
$X_1$ is a leucine, alanine, or absent,
$X_2$ is a lysine, proline, or absent,
$X_3$ is a leucine, an aspartic acid, tyrosine, phenylalanine, or absent,
AA is any amino acid, and n and p are integers between 0 and 2,
$R_1$ is the N-terminal amino acid's primary amine function, whether free or substituted with a group of the acyl type having a $C_1$ to $C_{30}$ alkyl chain, whether saturated or unsaturated, which is selected from an acetyl group or an aromatic group, where the latter is selected from a group of the benzoyl, tosyl, or benzyloxycarbonyl type,
$R_2$ is the hydroxyl group of the C-terminal amino acid's carboxyl function, whether free or substituted with a group that is selected from a $C_1$ to $C_{30}$ alkyl chain, or a $NH_2$, NHY or NYY group, where Y is a $C_1$ to $C_4$ alkyl chain,
said sequence of general formula (I) consisting of 5 to 12 amino acid residues, and where said sequence of general formula (I) can include derivatives or substitutions of the AA, $X_1$, $X_2$, or $X_3$ amino acids with other chemically equivalent amino acids.

The term "peptide compound" or "peptide" denotes a chain of two or more amino acids linked together by peptide bonds or modified peptide bonds.

By "peptide compound" or "peptide", is meant the naturally occurring or synthetic peptide according to the present invention as described above, or at least one of its fragments, whether obtained by proteolysis or synthetically, or also any naturally occurring or synthetic peptide whose sequence entirely or partially consists of the aforedescribed peptide sequence.

The amino acids constituting the peptide compound according to the present invention may be in the Levorotatory configuration, that is, L- and/or Dextrorotatory configuration, that is D-. The peptide according to the present invention can thus be in a L-, D- or DL-form.

In order to improve resistance to degradation, it may be necessary to use a protected form of the peptide of the invention. The form of protection must obviously be a biologically compatible form, and should be compatible with use in the fields of cosmetics and pharmacy. Preferably, to protect the N-terminal amino acid's primary amino function, a substitution with a group $R_1$ of the acyl type with a $C_1$ to $C_{30}$, saturated or unsaturated alkyl chain is used, which may be selected from an acetyl group or an aromatic group. Preferably, to protect the C-terminal amino acid's carboxyl function, substitution with a group $R_2$ of the $C_1$ to $C_{30}$ alkyl chain type, or a $NH_2$, NHY or NYY group, where Y is a $C_1$ to $C_4$ alkyl chain, is used.

The peptide according to the present invention can be protected at the N-terminal end, C-terminal end or at both ends.
In a first preferred embodiment, in formula (I),
$X_1$ is a leucine, or absent,
$X_2$ is a lysine, or absent,
$X_3$ is a tyrosine, or absent,
in AA, integers n and p are equal to zero,
$R_1$ is the N-terminal amino acid's primary amine function, whether free or substituted with a group of the acyl type having a $C_1$ to $C_{30}$ alkyl chain, whether saturated or unsaturated, which may be selected from an acetyl group or an aromatic group, where the latter can be selected from a group of the benzoyl, tosyl, or benzyloxycarbonyl type,
$R_2$ is the hydroxyl group of the C-terminal amino acid's carboxyl function, whether free or substituted with a group that can be selected from a $C_1$ to $C_{30}$ alkyl chain, or a $NH_2$, NHY or NYY group, where Y is a $C_1$ to $C_4$ alkyl chain.

In a second preferred embodiment, the peptide compound corresponds to one of the following formulas:

```
                                              (SEQ ID No 1)
Ile-Leu-Arg-Glu-Met-Asn-Trp-Gly-NH2

(SEQ ID No 2)
Arg-Glu-Met-Asn-Trp-NH2

(SEQ ID No 3)
Asp-Ala-Arg-Glu-Met-Asn-Trp-Asp-Thr (SEQ ID No 4)
Leu-Arg-Glu-Met-Asn-Trp-Tyr-NH2
```

```
                                                (SEQ ID No 5)
    Arg-Glu-Met-Asn-Trp-Phe-Met-Val (SEQ ID No 6)
    Leu-Lys-Arg-Glu-Met-Asn-Trp-Tyr-NH₂
```

The present invention also relates to homologous forms of these sequences. By "homologous", according to the present invention, is meant any peptide sequence which is identical to at least 50%, or preferably to at least 80%, and still more preferably to at least 90% of said peptide sequence, which is selected from sequences SEQ ID NO: 1 to SEQ ID NO: 6. By "peptide sequence identical to at least X %", is meant a percentage or similarity between the amino acid residues of the two sequences to be compared, obtained after optimum alignment of the two sequences. An optimum alignment is obtained using local homology algorithms such as those used in the BLAST P computer software available from the NCBI Web site.

The term "homologous" can also refer to a peptide, which differs from the sequence of a peptide of sequences SEQ ID NO: 1 to SEQ ID NO: 6 by the substitution of chemically equivalent amino acids, that is, by substituting a residue with another having the same characteristics. Conventional substitutions are thus performed between Ala, Val, Leu and Ile; between Ser and Thr; between acid residues Asp and Glu; between Asn and Gln; and between the basic residues Lys and Arg; or between the aromatic residues Phe and Tyr.

The peptide of general formula (I) according to the present invention can be obtained either by conventional chemical synthesis (in a solid phase or liquid homogeneous phase), or by enzymatic synthesis (Kullman et al., J. Biol. Chem. 1980, 225, 8234), from the constituent amino acids or derivatives thereof.

The peptide according to the present invention may be naturally occurring or synthetic. Preferably, according to the present invention, the peptide is obtained by chemical synthesis.

Lastly, the active ingredient may be a single peptide, a mixture of peptides, or peptide derivatives and/or consist of derivatives of amino acids.

The peptide compound according to the present invention can be used as a medication.

According to one advantageous embodiment of the present invention, the peptide compound according to the present invention is solubilized in one or more physiologically suitable solvents, conventionally used by those skilled in the art, such as water, ethanol, propanediol, butylene glycol, dipropylene glycol, ethoxylated or propoxylated diglycols, cyclic polyols, or any mixture of these solvents.

According to yet another advantageous embodiment of the present invention, the peptide compound according to the present invention is solubilized in a cosmetic or pharmaceutical vector such as liposomes, or adsorbed onto powdery organic polymers, mineral supports such as talcs and bentonites, and more generally dissolved in, or fixed to any physiologically suitable vector.

The peptide compound according to the present invention is characterized in that it allows the amount of Survivin protein and/or CPC activity to be modulated.

By peptide compound that "allows the amount of Survivin protein to be modulated" is meant any peptide or biologically active derivative capable of increasing or decreasing the activity of the CPC complex and/or Survivin, either by means of an increase or decrease in the synthesis of the CPC and/or Survivin proteins (by direct or indirect modulation of gene expression), or through other biological processes such as stabilization or non-stabilization of RNA messenger transcripts.

The second object of the present invention relates to a cosmetic composition comprising as the active ingredient said peptide compound of general formula (I).

Preferably, the compositions according to the present invention are in a form suitable for topical application comprising a cosmetically acceptable medium. By "cosmetically acceptable", are meant media that are suitable for use in contact with the skin or human keratinous appendages, without any risk of toxicity, incompatibility, instability, allergic response, and the like. The compositions intended to be applied to the skin can be in the form of a cream, oil-in-water or water-in-oil emulsions or multiple emulsions, a solution, suspension, micro-emulsion, aqueous or anhydrous gel, serum, or also a dispersion of vesicles, a patch, spray, ointment, pomade, emulsion, colloid, milk, lotion, stick, or also of a powder, all of which are suitable for application to the skin, lips and/or keratinous appendages.

Preferably, said peptide compound is present in the composition at a concentration of between about 0.0005 and 500 ppm, preferably at a concentration of between 0.01 and 5 ppm.

Still more preferably, the composition according to the present invention further contains at least one other active ingredient, which promotes the action of said peptide compound. Examples include, without limitation, the following classes of ingredients: other active peptide agents, plant extracts, healing, anti-aging, anti-wrinkle, soothing, free-radical scavenger, and anti-UV agents, agents that stimulate dermal macromolecule synthesis or energy metabolism, hydrating, anti-bacterial, anti-fungal, anti-inflammatory agents, anesthetics, agents that modulate skin differentiation, pigmentation or depigmentation, agents that stimulate nail or hair growth, etc. Preferably, an agent with anti-wrinkle activity, such as a free-radical scavenger or antioxidant agent, or an agent that stimulates dermal macromolecule synthesis, or also an agent that stimulates energy metabolism will be used. In particular, the active ingredient is selected from vitamins, phytosterols, flavonoids, DHEA and/or a precursor thereof or a chemical or biological derivative thereof, a metalloproteinase inhibitor or a retinoid.

In a more particular embodiment, the composition according to the present invention will comprise, besides the peptide compound of formula (I),
- one (or more) cytochrome c promoter compound; and/or
- one (or more) aquaporin promoter compound; and/or;
- one (or more) sirtuin promoter compound; and/or
- one (or more) compound stimulating cellular adhesion; and/or
- one (or more) compound increasing the production of matrix proteins of the collagen type, laminin, etc.;
- one (or more) compound modulating proteasome activity;
- one (or more) compound modulating the circadian rhythm;
- one (or more) compound modulating hsp proteins;
- one (or more) cellular energy increasing compound;
- one (or more) pigmentation modulating compound;
- one (or more) Coenzyme Q10 inducing compound;
- one (or more) compound improving the skin barrier function;
- one (or more) mitochondria protecting compound.

The above compounds can be naturally occurring, such as plant peptide hydrolysates or of synthetic origin, such as peptide compounds.

Additionally, additives such as solvents, thinners, dyes, sunscreens, self-tanning agents, pigments, fillers, preservatives, odor absorbers, thickeners, emulsifiers, humectants, emollients, perfumes, antioxidants, film-forming agents, chelating agents, sequestering agents, conditioners, . . . can be added to the composition.

In all cases, the person skilled in the art will ensure that these adjuvants as well as their proportions are chosen so as not to impair the advantageous properties sought for the composition according to the present invention. For example, these adjuvants can be present in an amount between 0.01 and 20% of the total weight of the composition. When the composition according to the present invention is an emulsion, the fatty phase can represent from 5 to 80% by weight and preferably, from 5 to 50% by weight of the total weight of the composition. The emulsifiers and co-emulsifiers used in the composition are selected from those conventionally used in the field. These can be used, for example, in an amount ranging between 0.3 and 30% by weight, with respect to the total weight of the composition.

A third object of the present invention relates to the use of a composition comprising a peptide compound according to the present invention, to restore an optimum level of Survivin in cells of the skin, hair and keratinous appendages, and to ensure better functioning of the "Chromosomal Passenger Complex". By "restore an optimum level of Survivin" is meant the ability of the inventive compound to increase or decrease the amount of Survivin protein present in skin cells, in particular epidermal and follicular adult stem cells, so that the latter can best control their mitoses, and thus best meet the needs for renewal of the epidermal cells.

Another object of the present invention relates to the use of a cosmetic composition comprising said peptide compound and a cosmetically acceptable medium to prevent and/or treat signs of skin aging and photo-aging, and promote tissue regeneration. The "signs of skin aging" include, but are not limited to, all conspicuous manifestations caused by the aging of the skin. In particular, this denotes wrinkles, deep and coarse wrinkles, fine lines, cracks, sagging of the cutaneous and sub-cutaneous tissues, loss of skin elasticity, and sluggishness, loss of firmness and tone, and dermal atrophy. Furthermore, by "signs of skin aging" are also meant enlarged pores, blemishes, discoloration, age spots, keratosis, collagen loss, and other changes in the dermis and epidermis, but also any changes in the external appearance of the skin, hair and nails due to aging, such as, for example, surface roughness of the stratum corneum, but also any internal modification of the skin which does not systematically translate into a modified external appearance, such as, for example, thinning of the dermis. By "photo-aging" is meant premature aging of the skin caused by prolonged and cumulative exposure to the sun.

By "tissue regeneration" is meant tissue reconstruction from one or more cells. The tissue regeneration process is involved, in particular, in wounds and healing. The peptide compound according to the present invention can promote this regeneration process, in particular by protecting the environment of the epidermal and follicular adult stem cells. Tests carried out in vitro have shown an increase in the expression of proteins that form the close environment specific to such stem cells. Proteins whose expression was increased are $\beta 1$-integrin, $\alpha 6$-integrin, keratin K15, as well as keratin K19, the latter being a keratin which is highly specific to the adult stem cells located in the hair bulb.

Another object of the present invention relates to the use of a composition according to the present invention to protect the skin against external aggressions, in particular those due to UV radiation. By "external aggressions" are meant aggressions that can be caused by the environment. Examples include aggressions such as pollution, UV radiation, or also irritating chemicals such as surfactants, preservatives or perfumes, mechanical aggressions, such as abrasion, shaving or depilation. Dryness of the atmosphere is also a major cause of cutaneous aggression. All of these phenomena lead to a reduction in the thickness of the basal layer. Since the latter is thinner and contains fewer epidermal adult stem cells, skin regeneration occurs in a less appropriate manner and aging accelerates. Tests carried out in vitro have shown that applying a composition comprising a peptide compound according to the present invention allowed the impact of aggressions, due to UV radiation of the cells that compose the basal layer, to be limited, whence the protective action of such compounds.

In a particularly preferred embodiment, the invention relates to the use of a composition comprising said peptide compound to prevent and/or limit hair loss, and/or stimulate hair growth. Tests carried out on biopsies of the skin and hair follicles have shown that the active ingredient according to the present invention has a protective action on the follicles, in particular upon exposure to UVA and UVB radiation. The compound according to the present invention thus exerts a protective action on the follicular cells against external aggressions, in particular against UV radiation.

Lastly, a final object of the present invention relates to a cosmetic treatment method, characterized in that a composition comprising an effective amount of the peptide compound according to the present invention is applied topically to the skin or keratinous appendages to be treated, in order to prevent and/or treat signs of skin aging and photo-aging and to promote tissue regeneration.

The following examples describe and demonstrate the efficacy of peptide compounds such as those described according to the present invention, but should not be construed as limiting the present invention.

EXAMPLE 1

Preparation of Cellular Fractions and Quantification of the Survivin Protein

To investigate the role of the CPC proteins in the maintenance and protection of epidermal adult stem cells under various types of stress, several fractions of primary cells of human epidermis were prepared. Fractioning was carried out based on the adhesion time of cells to collagen IV: less than 20 minutes corresponds to fast adhesion (fraction RA), less than 5 hours, to slow adhesion No 1 (fraction SA1), less than 16 hours, to slow adhesion No 2 (fraction SA2), and lastly, non-adhering keratinocytes (fractions NA). The cellular fraction RA contains the fastest-adhering, and thus less differentiated cells, and as a consequence, RA is that fraction which is enriched in epidermal adult stem cells. In contrast, fractions SA1, SA2 and NA are those containing fewer and fewer stem cells, respectively. Thereafter, Western Blotting was used to characterize Survivin protein levels.

Results:

Following this characterization, it is seen that Survivin is overexpressed in RA cells and that the expression levels gradually decrease in SA1, SA2 cells down to values close to zero in NA cells.

EXAMPLE 2

Demonstration of the Promoting Effect of Peptide SEQ ID NO: 2 on the Expression of the Survivin Protein in Cell Fractions RA and SA1

An investigation of the modulator effect of the peptide SEQ ID NO: 2 was conducted by evaluating the expression of the Survivin protein by Western Blotting on the cultured cellular fractions RA and SA1. The Western Blot technique is a conventional semi-quantitative method for assessing the proportion of proteins in cells.

Protocol

Fractions RA and SA1 were grown in boxes 100 mm in diameter at 37° C. in a humidified atmosphere containing 5% $CO_2$ for 48 hours with or without the compound, diluted to 3% (from a $10^{-4}$ M solution). The cells were rinsed and then detached from the carrier using an extraction buffer (25 mM Tris-HCl pH 7.6, 150 mM NaCl, 1% NP-40, 1% Sodium deoxycholate and 0.1% SDS) in the presence of a combination of protease inhibitors (Halt protease inhibitor PIERCE). The thus extracted proteins were centrifuged at 4° C. at 10,000 rpm for 10 minutes before being assayed using the BCA protein assay kit (Pierce). The cell lysates were mixed with a denaturation buffer and subjected to SDS-PAGE electrophoresis. The gel used is a 4-12% Nupage (invitrogen). The proteins were then transferred onto a membrane using an Iblot transfer machine (Invitrogen). The membranes were saturated with a 5% TBS-milk/0.1% Tween 20 for 2 hours at room temperature, and then incubated at 4° C. overnight with an anti-Survivin primary antibody to $\frac{1}{1000}^{th}$ (Cell signaling #2808-rabbit) followed by 3 washes in TBS, 0.1% Tween, followed by incubation with an anti-rabbit secondary antibody coupled with the peroxidase diluted to $\frac{1}{5000}^{th}$ (Immunotech). Development was carried out using a chemiluminescent substrate. The quantitative evaluation of the proteins in the cells is performed using the Chemiimager software (Alpha Innotech Corporation USA). The amount of proteins is expressed as a percentage of the light intensity compared with that of the control conditions, under which no treatment has been received.

Results:

The peptide SEQ ID v 2 allows the expression of the Survivin protein to be increased in those fractions that are very rich in epidermal adult stem cells (RA) as well as in those fractions that are less rich in epidermal adult stem cells (SA1).

EXAMPLE 3

Comets Test on Cellular Fraction RA

The comets test is a test that allows damage caused to DNA to be quantified at a cellular level.

To this end, in order to confirm the protective effect of a peptide compound according to the present invention, cells of the RA type were cultured for 24 hours with the peptide compound of sequence SEQ ID NO: 2 at a concentration of 1%, and then irradiated with UVB radiation at 60 $mJ/cm^2$. Control conditions were achieved with no peptide active ingredient present. The cells were then removed by trypsination from their carrier, and then centrifuged at 900 rpm for 5 minutes before being concentrated and counted.

A specific cell count (25,000 cells) was then incorporated into a 0.75% Low Melting agarose gel, and then deposited on a glass slide previously coated with 1% agarose. The slides were then immersed in a lysis solution for 1.5 hours at 4° C., and then in an alkaline solution for 20 minutes at 4° C. The cells were then lysed and the DNA denatured. The slides were immersed in an electrophoresis solution before applying an electric field (20 V-250 mA). The thus denatured DNA was subjected to migration within an agarose gel at 4° C. Applying a DNA fluorescent dye on the slides (2 µg/ml propidium iodide) allowed the DNA to be observed in the form of comets in those cases where it had been damaged.

Quantification software is used to determine the average Tail moment applied to each condition being tested. This parameter provides information on the level of DNA damage.

Figure 1:
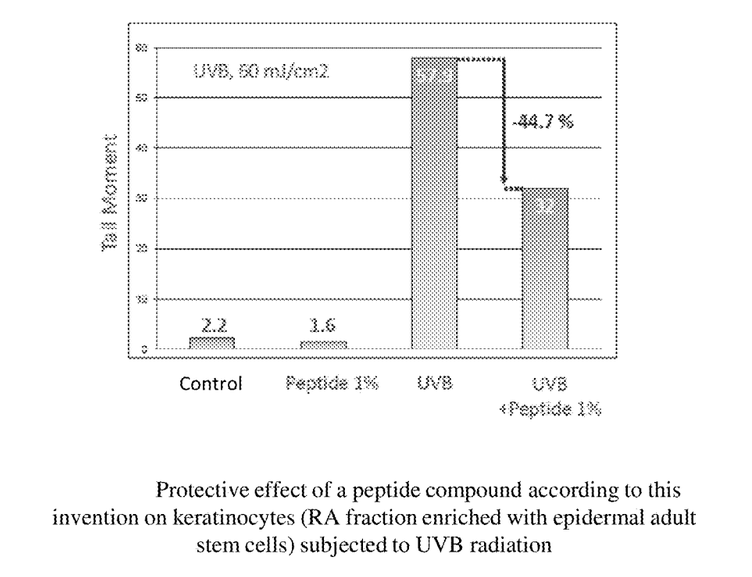
FIG. 1 is a histogram showing the results of a comets test carried out on a cellular fraction enriched with epidermal adult stem cells.

Results:

The results are shown in FIG. 1. The Tail Moment decreases by 44.7% when the peptide is applied, that is, the cells have suffered less damage than for the control conditions under which UVB radiation is applied. The results indeed confirm the protective effect of the peptide compound of SEQ ID NO: 2 on the cells derived from fractions enriched with epidermal adult stem cells (RA).

EXAMPLE 4

MITOSOX Test

Mitosox is a reactant marketed by Invitrogen (molecular probes M36008). It is used during UV and $H_2O_2$ oxidative stress. It uses microscopic imaging to measure the mitochondrial production of free radicals (ROS) in cells. More particularly, Mitosox is specific to the superoxide anion, which is the predominant form of ROS.

Mitosox is applied to living cells: it permeates the membrane and once inside the cell, diffuses rapidly and specifically within the mitochondria. Once in the mitochondria, Mitosox is oxidized by the superoxide anion into a compound which provides red fluorescence. This reactant is easily oxidized by the superoxide anion but not by other free radicals, nor by reactive species of nitrogen (NOS).

Protocol:

RA and TOTAL keratinocytes (where TOTAL denotes an entire cellular fraction) were treated three times per day with the peptide compound of SEQ ID NO: 3 at concentrations of 1% and 3%, for 48 hours.

In a second step, the cells were placed under stress, caused: either by exposure to 5 mM $H_2O_2$ solution for 30 minutes; or by UVB radiation at 100 $mJ/cm^2$.

After stress application, the cells were rinsed and then returned into a suitable medium for one hour at 37° C. in a culture incubator. Two washes were then performed using Hanks medium, the Mitosox solution was applied for 5 minutes and finally, new washings were performed using the same medium. The cells were fixed using formaldehyde for 10 minutes and DAPI was applied for 5 minutes, before two rinses with PBS. The results were read using fluorescence microscopy.

Results:

Using fluorescence microscopy, it was noted that under the control conditions, the number of cells having been damaged by both UV radiation and $H_2O_2$, was very high. Fluorescence was indeed very strong under these conditions, which indicates a high production of free radicals. In contrast, when the peptide was added to the cells before exposure to stress, it was noted that the number of fluorescent cells was extremely low. This implies that the peptide had protected the cells against excessive production of free radicals.

EXAMPLE 5

Action of the Peptide Compound SEQ ID NO: 2 on Hair Follicles Maintained in Culture and Marked with Keratin K19

Culture of Hair Follicles and Inclusions:

The hair follicles were sampled from a biopsy using a scalpel and fine pliers, and then cultured in 24-well plates using William's E medium in the presence of antibiotics (0.2% Primocin), 10 µg/ml insulin, 10 ng/ml hydrocortisone and 2 mmol/L L-glutamine.

The follicles were either treated or not with the 1% peptide compound SEQ ID NO: 2 in Williams' medium and then incubated for 24 hours. UV irradiation was then applied (UVA: 5 J/cm, UVB 200 mJ/cm$^2$), and the follicles were then re-cultured for 24 hours. At the end of the experiment, the follicles were incorporated within OCT and frozen at −196° C. (liquid nitrogen). The follicles were then placed in a cryostat in order to prepare 6-µm sections at a temperature of −23° C. The slides containing the sections were placed in an acetone bath for 10 minutes (fixing) and then rinsed.

Immunolabeling of Keratin K19:

The fixed sections were rinsed once with PBS for 5 minutes, and then wrapped in Pappen. Each section was incubated with 5 µl 5%-BSA for 30 minutes. Then, 50 µl of primary anti-Cytokeratin K19 antibody (Progen, Mouse monoclonal) diluted to 1/50$^{th}$ were added and incubated for one hour with stirring in a humid chamber. After rinsing with PBS for 30 minutes, 50 µl of a fluorescence-labeled secondary antibody was added and left for one hour in the dark with stirring in a humid chamber. The slides were then rinsed in PBS, mounted between a slide and coverslip in Fluoromount G, and the observation was carried out using an epifluorescence microscope.

Results:

UV irradiation of follicles resulted in a −48% decrease in fluorescence intensity of Keratin K19 in said hair follicles (quantification performed by image analysis). The follicles that were treated with the peptide compound SEQ ID NO: 2 before irradiation had fluorescent values of Keratin K19 of +102.7%. This means that the peptide compound according to the present invention allowed the appearance of damage in the cells to be prevented and avoided, in particular in terms of keratin K19 production.

EXAMPLE 6

Compositions

1. Composition of a Sunscreen

| Trade names | INCI Names | wt % |
|---|---|---|
| | PHASE A | |
| Demineralized water | Aqua (Water) | qsp |
| PEMULEN ™ TR1 | Acrylates/C10-30 Alkyl Acrylate Crosspolymer | 0.40 |
| Glycerin | Glycerin | 3.00 |

-continued

| Trade names | INCI Names | wt % |
|---|---|---|
| NIPASTAT ® Sodium | Sodium Methylparaben (and) Sodium Ethylparaben (and) Sodium Butyl paraben (and) Sodium Propylparaben (and) Sodium Isobutylparaben | 0.15 |
| | PHASE B | |
| PARSOL ® MCX | Ethylhexyl Methoxycinnamate | 7.50 |
| EUSOLEX ® 4360 | Benzophenone-3 | 3.00 |
| PARSOL ® 1789 | Butyl Methoxydibenzoylmethane | 2.00 |
| MYRITOL ® 318 | Caprylic/Capric Triglyceride | 4.00 |
| EMULGADE ® SEV | Hydrogenated Palm Glycerides (and) Ceteareth-20 (and) Ceteareth-12 (and) Cetearyl Alcohol | 5.00 |
| Propylparaben | Propylparaben | 0.15 |
| NACOL ®16-98 | Cetyl Alcohol | 1.00 |
| | PHASE C | |
| TEA | Triethanolamine | 0.20 |
| | PHASE D | |
| Peptide SEQ ID No 2 | | 3 ppm |
| Fragrance | Fragrance | qsp |
| Dye | | qsp |

2. Hair Growth Serum

Disperse the NATROSOL® 250HHR hydroxyethylcellulose and Disodium EDTA in water with stirring. Heat to 50-60° C. and stir until a uniform appearance is achieved. Add STYLEZE® CC-10 polymer and stir until a uniform appearance is achieved. Allow to cool to room temperature and add the ingredients in the order shown in the list with stirring until a uniform appearance is obtained between each of them.

| INCI Name | Trade Name | wt % | Provider |
|---|---|---|---|
| Water | | qsp | |
| Hydroxyethylcellulose | NATROSOL ® 250HHR hydroxyethylcellulose | 0.35 | Hercules/Aqualon |
| Disodium EDTA | DISSOLVINE ® NA-2S sequestering agent | 0.05 | Akzo Nobel |
| VP/DMAPA Acrylates Copolymers | STYLEZE ® CC-10 polymer | 5.00 | ISP |
| Quaternium-26 | CERAPHYL ® 65 emollient | 1.00 | ISP |
| Panthenol | Ritapan DL | 0.15 | RITA |
| Propylene Glycol Diazolidinyl Urea Iodopropynyl Butylcarbamate | LIQUID GERMALL ® Plus preservative | 0.50 | ISP |
| Peptide SEQ ID NO: 5 | | 2 ppm | ISP |
| Total | | 100.00 | |

The invention claimed is:

1. A peptide compound of the following general formula (I):

$$R_1\text{-}(AA)_n\text{-}X_1\text{—}X_2\text{-Arg-Glu-Met-Asn-Trp-}X_3\text{-}(AA)_p\text{-}R_2$$

where
- $X_1$ is a leucine, alanine, or absent,
- $X_2$ is a lysine, proline, or absent,
- $X_3$ is a leucine, aspartic acid, tyrosine, phenylalanine, or absent,
- AA is any amino acid, and n and p are integers between 0 and 2,
- $R_1$ is the N-terminal amino acid's primary amine function, whether unsubstituted or substituted with group of the acyl type having a $C_1$ to $C_{30}$ alkyl chain, whether saturated or unsaturated, which is selected from an acetyl group or an aromatic group, where the latter is selected from a group of the benzoyl, tosyl, or benzyloxycarbonyl type,
- $R_2$ is the hydroxyl group of the C-terminal amino acid's carboxyl function, substituted with a group that is selected from a $C_1$ to $C_{30}$ alkyl chain, or a $NH_2$, NHY or NYY group, where Y is a $C_1$ to $C_4$ alkyl chain, said sequence of general formula (I) consisting of 5 to 12 amino acid residues.

2. The peptide compound according to claim 1, wherein in the general formula (I)
- $X_1$ is a leucine, or absent,
- $X_2$ is a lysine, or absent,
- $X_3$ is a tyrosine, or absent,
- in AA, the integers n and p are equal to zero,
- $R_1$ is the N-terminal amino acid's primary amine function, whether unsubstituted or substituted with a group of the acyl type having a $C_1$ to $C_{30}$ alkyl chain, whether saturated or unsaturated, which is selected from an acetyl group or an aromatic group, where the latter is selected from a group of the benzoyl, tosyl, or benzyloxycarbonyl type,
- $R_2$ is the hydroxyl group of the C-terminal amino acid's carboxyl function, substituted with a group that is selected from a $C_1$ to $C_{30}$ alkyl chain, or a $NH_2$, NHY or NYY group, where Y is a $C_1$ to $C_4$ alkyl chain.

3. The peptide compound according to claim 1, wherein the peptide is selected from the group consisting of the following sequences:

Ile-Leu-Arg-Glu-Met-Asn-Trp-Gly-NH$_2$; (SEQ ID No 1)

Arg-Glu-Met-Asn-Trp-NH$_2$; (SEQ ID No 2)

Asp-Ala-Arg-Glu-Met-Asn-Trp-Asp-Thr-NH$_2$; (SEQ ID No 3)

Leu-Arg-Glu-Met-Asn-Trp-Tyr-NH$_2$; (SEQ ID No 4)

Arg-Glu-Met-Asn-Trp-Phe-Met-Val-NH$_2$; (SEQ ID No 5)

and

Leu-Lys-Arg-Glu-Met-Asn-Trp-Tyr-NH$_2$. (SEQ ID No 6)

4. The peptide compound according to claim 1, wherein the peptide is solubilized in one or more physiologically acceptable solvents, selected from the group consisting of water, glycerol, ethanol, propanediol, butylene glycol, dipropylene glycol, ethoxylated or propoxylated diglycols, cyclic polyols, and combinations thereof.

5. A cosmetic composition, comprising as an active ingredient, the peptide compound according to claim 1.

6. The composition according to claim 5, being in a form suitable for topical application, comprising a cosmetically acceptable medium.

7. The composition according to claim 5, wherein said peptide compound is present in the composition at a concentration of between about 0.0005 and 500 parts per million (ppm).

8. The composition according to claim 5, further comprising at least one other active ingredient which promotes the action of said peptide compound, the other active ingredient selected from the group consisting of vitamins, phytosterols, flavonoids, dehydroepiandrosterone (DHEA), a metalloproteinase inhibitor, a retinoid, and combinations thereof.

9. The composition according to claim 7, wherein said peptide compound is present in the composition at a concentration of between about 0.01 and 5 ppm.

10. A method of restoring an optimum level of Survivin in the cells of the skin, hair and keratinous appendages, and to ensure better functioning or the "Chromosomal Passenger Complex" (CPC) comprising:
applying on at least one of skin, hair, and keratinous appendages a cosmetic composition comprising the peptide compound as defined in claim 5, and a cosmetically acceptable medium.

11. The method according to claim 10, wherein applying occurs before exposure to ultraviolet (UV) radiation.

12. A method of cosmetic treatment, comprising:
topically applying onto the skin or keratinous appendages to be treated, in the morning and/or evening, a composition comprising an effective amount of the peptide compound as defined in claim 1, in order to treat the signs of skin aging and photo-aging, promote tissue regeneration, treat hair loss, and/or promote hair growth.

13. The method according to claim 12, wherein the signs of skin aging comprise wrinkles, deep and coarse wrinkles, fine lines, cracks, sagging of cutaneous and sub-cutaneous tissues, loss of skin elasticity, and sluggishness, loss of firmness and tone, and/or dermal atrophy.

14. The method according to claim 12, wherein promoting hair growth includes stimulating the growth of eyebrows.

\* \* \* \* \*

SEQUENCE LISTING

<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)

```
<223> OTHER INFORMATION: AMIDATION

<400> SEQUENCE: 1

Ile Leu Arg Glu Met Asn Trp Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 2

Arg Glu Met Asn Trp
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 3

Asp Ala Arg Glu Met Asn Trp Asp Thr
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: AMIDATION

<400> SEQUENCE: 4

Leu Arg Glu Met Asn Trp Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 5

Arg Glu Met Asn Trp Phe Met Val
1               5

<210> SEQ ID NO 6
<211> LENGTH: 8
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 6

Leu Lys Arg Glu Met Asn Trp Tyr
1               5
```